United States Patent
Levine

(10) Patent No.: US 7,335,025 B2
(45) Date of Patent: Feb. 26, 2008

(54) METHOD OF TOOTH WHITENING INCLUDING WRAPPING THE TEETH

(75) Inventor: Jonathan B. Levine, Purchase, NY (US)

(73) Assignee: Gosmile, Inc., New York, NY (US)

( * ) Notice: Subject to any disclaimer, the term of this patent is extended or adjusted under 35 U.S.C. 154(b) by 0 days.

(21) Appl. No.: 11/346,249

(22) Filed: Feb. 3, 2006

(65) Prior Publication Data

US 2007/0122769 A1 May 31, 2007

Related U.S. Application Data

(60) Provisional application No. 60/739,921, filed on Nov. 28, 2005.

(51) Int. Cl.
*A61C 5/00* (2006.01)
*A61C 15/00* (2006.01)

(52) U.S. Cl. ...................................... 433/215; 433/216

(58) Field of Classification Search ................ 433/215, 433/216

See application file for complete search history.

(56) References Cited

U.S. PATENT DOCUMENTS 6,884,426 B2 * 4/2005 Sagel et al. ................. 424/401

* cited by examiner

*Primary Examiner*—Cris Rodriguez
*Assistant Examiner*—Candice C Stokes

(57) ABSTRACT

In the inventive method, a tooth whitener having a concentration of hydrogen peroxide significantly lower than the concentration typically used in in-office applications is applied to the teeth in gel form. Next, thin transparent film is placed over the teeth to seal the tooth whitener onto the teeth. The film creates a closed system that precludes oxygen from migrating away from the teeth into the atmosphere. A white light in the range of 380-660 nm wavelength is then activated to assist in exciting oxygen in the path of the light and the oxygen molecules bombard the tooth surfaces. The oxygen molecules may not easily escape from the tooth surfaces into the atmosphere due to the wrap and, thus, their whitening "power" is enhanced and lengthened. Then, the patient may stabilize the whitening results over a 7 to 10 day regime using a lower concentration tooth whitener.

15 Claims, No Drawings

US 7,335,025 B2

METHOD OF TOOTH WHITENING INCLUDING WRAPPING THE TEETH

BACKGROUND OF THE INVENTION

The present invention relates to a method of tooth whitening including wrapping the teeth. The present application claims priority from Provisional application No. 60/739,921, filed Nov. 28, 2005.

In the prior art, it is well known for a professional dental office to perform tooth whitening services for its patients. Typically, such services involve a 90 minute appointment involving use of a tooth whitener having a high concentration of hydrogen peroxide such as in the range of 18-35%. The whitener is placed on the teeth in three to four passes and a white light such as is generated by laser, halogen or zenon lights in the range of 380 nm to 660 nm is used. The white light helps to excite the oxygen on which the light shines and the excited oxygen molecules bombard the teeth. In the in-office whitening technique, the majority of the oxygen is released into the atmosphere rather than onto to the teeth while the tooth whitening takes place. Thus, such techniques are inherently inefficient.

Additionally, gels are placed on the teeth with a tray, whereby the leading edge of the gel is touching the tooth, while most of the gel is not contacting. The gel that is behind the leading edge that is touching the teeth never reaches the enamel surface.

Given the high concentration of hydrogen peroxide in the tooth whitener, only dental professionals are qualified and licensed to perform such tooth whitening services. Given the high concentration of hydrogen peroxide and the application of the white light in the manner typically done, the patient often exhibits major discomfort for the ensuing 24 hours. The high concentration tooth whitener often bleeds onto the gums and mucosa with resultant pain experienced by the patient.

Additionally, results from in-office tooth whitening are typically short lived since the contact time is short, typically 90 minutes. Thus, often, results from in-office tooth whitening regress in the first month and studies have shown that this regression can commence in as little as 7 days from completion of the in-office tooth whitening procedure.

It would be advantageous if it were possible to employ a tooth whitening technique that required a lower concentration of hydrogen peroxide in the whitener to reduce pain, facilitated concentration of the whitening effects of the whitener on the teeth for a shorter period of time than is now the case, and the "leading edge" of the whitener were greatly increased. It is with these thoughts in mind that the present invention was developed.

SUMMARY OF THE INVENTION

The present invention relates to a method of tooth whitening including wrapping of the teeth. The present invention includes the following interrelated objects, aspects and features:

(1) In a first aspect, the inventive method contemplates use of a tooth whitener having a concentration of hydrogen peroxide significantly lower than the concentration typically used in in-office applications. As explained above, typical such concentrations fall within the range of 18-35% hydrogen peroxide in the mixture of tooth whitening gel. In accordance with the teachings of the present invention, the percent concentration of hydrogen peroxide preferably falls within the range of 6-14%.

(2) One tooth whitener Applicant has found to be effective in practicing the teachings of the present invention is known by the trademark PEROXYDONE®. In the preferred embodiment of the present invention, PEROXYDONE® tooth whitener is vacuum packed within an ampule and the ampule is opened just prior to application, whereupon the fresh tooth whitener is applied over the surfaces of the teeth.

(3) Once the tooth whitener has been applied on the surfaces of the teeth, immediately, a thin film is placed over the teeth that are coated with the tooth whitener to seal the tooth whitener onto the teeth. The film creates a closed system that substantially precludes oxygen, the active ingredient of a tooth whitener, from migrating away from the teeth into the atmosphere. The film creates a closed chamber closely surrounding the teeth to facilitate concentrating of the tooth whitener onto the tooth surfaces. Prior art tooth whitening systems exhibit a rapid reduction of tooth whitener concentration through dilution with saliva, evaporation and other effects. The thin film isolates the tooth whitener from the saliva to preclude dilution in that way. The thin film also precludes evaporation by enclosing the tooth whitener as coated onto the teeth. The film placed over the teeth compresses the gel into the teeth, thus eliminating "leading edge" problem and maximizing the contact area of the active ingredients on the tooth's enamel.

(4) In the preferred embodiments of the present invention, the film used to enclose the teeth and the tooth whitener may be made of any type of transparent polypropylene, polyethylene or, if desired, SARAN® wrap, a well known thin film. Additionally, if desired, the film may be made of a material including a mixture with PEROXYDONE®. When this technique is employed, the film itself provides additional active ingredient while at the same time enclosing the tooth surfaces in a "chamber" precluding dilution of the tooth whitener and its evaporation. Where a PEROXYDONE® film is employed, the outer surfaces of the film may be sealed in any desired way, such as by an impervious coating or a plastic film, for example. The film may be a film such as is disclosed in U.S. Pat. No. 6,824,829 to Berry et al.

(5) Once the film has been placed over the teeth as coated by the tooth whitener, a white light in the range of 380-660 nm wavelength may be activated to shine the white light onto the tooth whitener through the film. As in the prior art, the white light assists in exciting oxygen in the path of the light and the oxygen molecules bombard the tooth surfaces. However, as compared to the prior art, when the white light is shone on the teeth, in accordance with the teachings of the present invention, the oxygen molecules may not easily escape from the tooth surfaces into the atmosphere and, thus, their whitening "power" is enhanced and lengthened. With the compression of the whitening gel on the teeth, closed system and no active oxygen escaping, the whitening time is greatly decreased. A preferred regimen is: 7.5% peroxide onto the teeth, PEROXYDONE® impregnated film sealing the teeth, white light at 380 nm shone onto the teeth through the film, placed 2 inches from teeth for 8 minutes. Active ingredient is removed and technique is repeated.

(6) Once the inventive technique has been employed, the patient may stabilize the whitening results over a 7 to 10 day regime using a lower concentration tooth whitener such as GoSMILE's B1 Advanced Whitening System. If the patient so desires, the B1 Advanced Whitening System or other tooth whitener may be applied with subsequent application of a thin film to enclose the whitener over the teeth.

As such, it is a first object of the present invention to provide a method of tooth whitening including wrapping the teeth.

It is a further object of the present invention to provide such a method in which a relatively lower concentration hydrogen peroxide based tooth whitener is employed and coated onto tooth surfaces.

It is a still further object of the present invention to provide such a method in which after the tooth whitener is coated onto the tooth surfaces, a thin film is wrapped over those tooth surfaces to create a chamber enclosing the tooth surfaces with the tooth whitener coated thereon.

It is a still further object of the present invention to provide such a method in which a bright white light is shone over the tooth surfaces as enclosed by the thin film which in the preferred embodiment is transparent.

It is a still further object of the present invention to provide such a method in which a maintenance whitening is carried out after the wrap is removed over a period of at least a week to 10 days.

These and other objects, aspects and features of the present invention will be better understood from the following detailed description of the preferred embodiments.

SPECIFIC DESCRIPTION OF THE PREFERRED EMBODIMENTS

In practicing the inventive method, first, a tooth whitener is provided in gel form such as, for example, GoSmile's B-1 system including a tooth whitener known by the name PEROXYDONE® that has a hydrogen peroxide concentration of 6.5-7.5%. Where PEROXYDONE® whitener is the whitener of choice, the whitener includes the following constituent ingredients: by weight, 80-83% of water soluble polyvinylpyrrolidone (PVP), e.g., K-15/K-30/K-90, and 17-20%, by weight, hydrogen peroxide ($H_2O_2$). Preferably, the whitener consists of 15-99% PEROXYDONE®, 0.2-1% oil of wintergreen, and the balance ethanol.

Of course, other tooth whitening substances may suitably be used in practicing the teachings of the present invention so long as the objects of the present invention are suitably met. Thus, preferably, whatever tooth whitener is employed is in a gel form to enhance retention on the surfaces of the teeth being whitened.

Preferably, the tooth whitener is vacuum packed within an ampule sized to contain a single dose of tooth whitener. When it is desired to apply the tooth whitener to the teeth, the ampule is broken open and the tooth whitener is dispensed onto the teeth by any suitable means. Although a brush is one preferred means of applying the tooth whitener, other means may also be employed such as a foam pad, a sponge or a cloth.

Once the tooth whitener is applied over the surfaces of the teeth, immediately, a transparent thin film is adhered over the surfaces of the teeth to enclose the tooth whitener in a chamber formed between the thin film and the tooth surfaces. The film creates a closed system that substantially precludes oxygen, the active ingredient of the tooth whitener, from migrating away from the teeth into the atmosphere. Thus, the tooth whitener is maintained in concentrated form on the surfaces of the teeth and is precluded from diluting through isolation from saliva and prevention of evaporation, among other effects. Additionally, the active gel is compressed by the film to avoid the "leading edge" effect and ensure contact area of the active.

In the preferred embodiment of the present invention, the film used to enclose the teeth and the tooth whitener may be of any type of material such as, for example, polypropylene, polyethylene or, if desired, SARAN® wrap. Additionally, if desired, the film may itself be made of a material including a mixture with PEROXYDONE®. When PEROXYDONE® is impregnated into the film, this results in enhanced concentration of tooth whitener on the surfaces of the teeth as well as increased length of time that the concentration of tooth whitener is present on the tooth surfaces.

In a further embodiment, the thin film may consist of a film such as is disclosed in U.S. Pat. No. 6,824,829 to Berry et al. The film disclosed in the Berry et al. patent is consumed in use, dissolving on the tooth surfaces. Thus, when impregnated with a tooth whitener such as, for example, one including a mixture including PEROXYDONE®, such as that of the B-1 system described above and below, enhanced whitening results due to the combination of sealing the teeth with a thin film in which the thin film is impregnated with a tooth whitener, thereby increasing the concentration of active ingredient.

Once the thin film has been placed over the teeth as coated by the tooth whitener, a white light in the range of 380-660 nm wavelength may be activated to shine white light onto the tooth whitener through the preferably transparent film. The white light assists in exciting oxygen in the path of the light as the oxygen molecules bombard the tooth surfaces. However, as explained above, the significant improvement over the prior art is that, as compared to the prior art, the oxygen molecules cannot easily escape from the tooth surfaces due to the enclosure by the thin film. Thus, excitation of the oxygen molecules by the white light enhances the tooth whitening process. After a desired period of time, as disclosed herein, the wrap is removed and the whitener is rinsed off the teeth with any desired rinse fluid such as water. The use of white light is preferred but not essential, since improvement over the prior art occurs through use of the thin film.

Once the tooth whitening process as explained above has been completed, the whitening results may be stabilized over, for example, a 7-10 day regime using a lower concentration tooth whitener of any desired kind or type. One example of such a tooth whitener is known as GoSMILE's B-1 Advanced Whitening System at the lower end of the hydrogen peroxide concentration range. The B-1 system has the following ingredients: 15-99% PEROXYDONEO®, 0.2-1% oil of wintergreen, and the balance ethanol. PEROXYDONE® is a Trademark of International Specialty Products (ISP) and is made up of, by weight, 80-83%, of water soluble polyvinylpyrrolidone (PVP), e.g. K-15/K-30/K-90, and 17-20%, by weight, hydrogen peroxide ($H_2O_2$). If desired, this maintenance regime may be enhanced through the use of a thin film in the manner explained above.

EXAMPLE 1

The teeth of a patient were whitened in accordance with the teachings of the present invention including use of a tooth whitener having the following formula: 90% PEROXYDONE®, 0.6% wintergreen, and the balance ethanol. After the tooth whitener was applied to the patient's teeth, a film made of the thin film disclosed in U.S. Pat. No. 6,824,829 to Berry et al. was impregnated with the B-1 system whitener described above and was placed over the teeth to seal the tooth whitener as applied to the teeth within a sealed chamber. A white light having a wavelength of 380 nm was activated for 10 minutes on the teeth. Activation of the white light was repeated for a second 10 minute period. Before the process was commenced, the patient's teeth exhibited a shade known as A-3 on the Vita scale. After completing the initial process, the patient's teeth exhibited a movement of 4 shades to shade A-1. Thereafter, a GoSMILE B-1 Maintenance Tooth Whitener was employed daily for 10 days and, after the 10 day period, the patient's teeth had a shade of B-1. The maintenance tooth whitener had the following ingredients: 6.5%, by weight, PEROXYDONE®, 0.6% wintergreen, and the balance ethanol.

EXAMPLE 2

The teeth of a patient were whitened in accordance with the teachings of the present invention including use of a tooth whitener having the following formula: 80% PEROXYDONE®, 0.6% wintergreen, and the balance ethanol. After the tooth whitener was applied to the patient's teeth, a thin film made of the thin film disclosed in U.S. Pat. No. 6,824,829 to Berry et al. was impregnated with the B-1 system whitener described above and was placed over the teeth to seal the tooth whitener as applied to the teeth within a sealed chamber. A white light having a wavelength of 660 nm was activated for 8 minutes on the teeth. Activation of the white light was repeated for another 8 minute period. Before the process was commenced, the patient's teeth exhibited a shade known as A-3, 5 on the Vita scale. After completing the initial process, the patient's teeth exhibited a movement of 5 shades to shade A-2. Thereafter, a GoSMILE B-1 Maintenance Tooth Whitener was employed daily for 10 days and, after the 10 day period, the patient's teeth had a shade of B-1. The B-1 maintenance whitener had the following ingredients: 7.8%, by weight, PEROXYDONE®, 0.6% wintergreen, and the balance ethanol.

If desired, the maintenance whitening that is undertaken by the patient for the ensuing 7 to 10 days may be undertaken twice a day. This procedure stabilizes the results achieved from in-office whitening.

The present invention is unique in that, through its use: (1) active Oxygen can't dissipate in the air, (2) the wrap film may contain the active whitening ingredients, thereby doubling the dosage while eliminating the "leading edge" effect, and (3) whitening time is shortened by as much as ⅔, from as much as 90 minutes to as little as 30 minutes.

As such, an invention has been disclosed in terms of preferred embodiments that fulfill each and every one of the objects of the invention as set forth hereinabove and provide a new and useful method of tooth whitening including wrapping the teeth, of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A method of tooth whitening, including the steps of:
   a) applying a tooth whitener to at least one tooth of a patient;
   b) enclosing said tooth and whitener within a flexible transparent wrap to create a chamber containing said tooth and whitener, then shining a light onto said tooth through said wrap for a desired time period;
   c) maintaining said wrap enclosing said tooth and whitener for a desired period of time;
   d) removing said wrap; and
   e) rinsing said whitener off said tooth.

2. The method of claim 1, wherein said at least one tooth comprises a plurality of teeth.

3. The method of claim 1, wherein said light comprises a white light having a wavelength of 380-660 nm.

4. The method of claim 3, wherein said white light is shone on said tooth for a period of 10 minutes.

5. The method of claim 4, wherein after said 10 minute period, said white light is shone on said teeth for a second 10 minute period.

6. The method of claim 1, wherein said flexible wrap is made of a material chosen from the group consisting of polypropylene, polyethylene, SARAN® wrap, and an edible material.

7. The method of claim 1, wherein said tooth whitener includes 15-99%, by weight, of a substance made up of, by weight, 80-83% water-soluble polyvinylpyrrolidone and 17-20% hydrogen peroxide; 0.2-1%, by weight, oil of wintergreen, and balance ethanol.

8. The method of claim 1, wherein said tooth whitener comprises a gel.

9. A method of tooth whitening, including the steps of:
   a) applying a gel tooth whitener to a patient's teeth;
   b) enclosing said teeth and whitener within a transparent flexible wrap to create a chamber containing said teeth and whitener;
   c) maintaining said wrap enclosing said teeth and whitener for a desired period of time;
   d) during said desired period of time, shining a white light on said teeth through said transparent wrap;
   e) removing said wrap; and
   f) rinsing said whitener off said teeth.

10. The method of claim 9, wherein said white light has a wavelength of 380-660 nm.

11. The method of claim 9, wherein said desired period of time comprises a first 10 minute period followed by a second 10 minute period.

12. The method of claim 9, wherein said tooth whitener includes 15-99%, by weight, of a substance made up of, by weight, 80-83% water-soluble polyvinylpyrrolidone and 17-20% hydrogen peroxide; 0.2-1%, by weight, oil of wintergreen, and balance ethanol.

13. The method of claim 12, wherein said flexible wrap is made of a material chosen from the group consisting of polypropylene, polyethylene, SARAN® wrap, and an edible material.

14. The method of claim 9, wherein said flexible wrap is made of a material chosen from the group consisting of polypropylene, polyethylene, SARAN® wrap, and an edible material.

15. A method of tooth whitening, including the steps of:
   a) applying a tooth whitener to at least one tooth of a patient, said tooth whitener including 15-99%, by weight, of a substance made up of, by weight, 80-83% water-soluble polyvinylpyrrolidone and 17-20% hydrogen peroxide; 0.2-1%, by weight, oil of wintergreen, and balance ethanol;
   b) enclosing said tooth and whitener within a flexible wrap to create a chamber containing said tooth and whitener;
   c) maintaining said wrap enclosing said tooth and whitener for a desired period of time;
   d) removing said wrap; and
   e) rinsing said whitener off said tooth.

* * * * *